US010054676B2

(12) United States Patent
Sinha et al.

(10) Patent No.: US 10,054,676 B2
(45) Date of Patent: Aug. 21, 2018

(54) ACOUSTIC CAMERA

(71) Applicant: LOS ALAMOS NATIONAL SECURITY, LLC, Los Alamos, NM (US)

(72) Inventors: Dipen N. Sinha, Los Alamos, NM (US); John F. Brady, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 709 days.

(21) Appl. No.: 14/398,367

(22) PCT Filed: Mar. 13, 2013

(86) PCT No.: PCT/US2013/030753
§ 371 (c)(1),
(2) Date: Oct. 31, 2014

(87) PCT Pub. No.: WO2013/165569
PCT Pub. Date: Nov. 7, 2013

(65) Prior Publication Data
US 2015/0124558 A1 May 7, 2015

Related U.S. Application Data

(60) Provisional application No. 61/641,969, filed on May 3, 2012.

(51) Int. Cl.
*G03B 42/06* (2006.01)
*G01S 7/52* (2006.01)
(Continued)

(52) U.S. Cl.
CPC ...... *G01S 7/52017* (2013.01); *G01N 29/0654* (2013.01); *G01N 29/07* (2013.01);
(Continued)

(58) Field of Classification Search
None
See application file for complete search history.

(56) References Cited

U.S. PATENT DOCUMENTS 3,345,909 A * 10/1967 De Maria ............. G01C 19/66
356/28
3,790,281 A * 2/1974 Kessler ............. G01N 29/0609
356/72
(Continued)

FOREIGN PATENT DOCUMENTS

DE      3545379          6/1987
DE      3545379 A1 *     6/1987  ............. G01H 3/005
(Continued)

OTHER PUBLICATIONS

Dipen Sinha. WO 2013/165569 A1. PCT/US2013/030753. Written Opinion and Search Report. pp. 1-44.*
(Continued)

*Primary Examiner* — Isam A Alsomiri
*Assistant Examiner* — Jonathan D Armstrong
(74) *Attorney, Agent, or Firm* — Samuel M. Freund; Cochran Freund & Young LLC

(57) ABSTRACT

Apparatus for generating accurate 3-dimensional images of objects immersed in liquids including optically opaque liquids which may also have significant sound attenuation, is described. Sound pulses are caused to impinge on the object, and the time-of-flight of the reflected sound is used to create a 3-dimensional image of the object in almost real-time. The apparatus is capable of creating images of objects immersed in fluids that are optically opaque and have high sound attenuation at resolutions less than about 1 mm. The apparatus may include a piezoelectric transducer for generating the acoustic pulses; a high-density polyethylene compound acoustic lens, a 2-dimensional segmented piezoelectric detecting array positioned behind the lens for receiving
(Continued)

acoustic pulses reflected by the object, the electric output of which is directed to digital signal processing electronics for generating the image.

19 Claims, 9 Drawing Sheets

(51) Int. Cl.
  *G01N 29/22* (2006.01)
  *G01N 29/06* (2006.01)
  *G01N 29/07* (2006.01)
  *G01S 15/89* (2006.01)
  *G01S 15/02* (2006.01)

(52) U.S. Cl.
  CPC ............ *G01N 29/221* (2013.01); *G01S 15/02* (2013.01); *G01S 15/8913* (2013.01); *G01S 15/8925* (2013.01); *G01S 15/8993* (2013.01); *G01N 2291/106* (2013.01)

(56) References Cited

U.S. PATENT DOCUMENTS

| | | | |
|---|---|---|---|
| 3,829,827 A * | 8/1974 | Ernvein | G01H 9/002 359/901 |
| 4,834,106 A * | 5/1989 | Hassler | A61B 8/00 600/439 |
| 5,072,091 A * | 12/1991 | Nagata | B23K 26/06 219/121.68 |
| 5,370,120 A | 12/1994 | Oppelt et al. | |
| 5,483,963 A | 1/1996 | Butler et al. | |
| 6,356,846 B1 * | 3/2002 | Habeger, Jr. | G01H 9/00 702/103 |
| 6,651,502 B1 | 11/2003 | Davis | |
| 2001/0042410 A1 * | 11/2001 | Ogawa | B82Y 15/00 73/656 |
| 2002/0009103 A1 * | 1/2002 | Toida | G01H 9/00 372/28 |
| 2002/0017141 A1 * | 2/2002 | Satoh | G01H 9/002 73/655 |
| 2002/0167974 A1 * | 11/2002 | Kennedy | H01S 3/2232 372/10 |
| 2003/0184753 A1 | 10/2003 | Ogawa | |
| 2004/0118210 A1 | 6/2004 | Tooma et al. | |
| 2005/0027198 A1 | 2/2005 | Couvillon | |
| 2005/0150309 A1 * | 7/2005 | Beard | A61B 5/0095 73/861.18 |
| 2007/0157730 A1 * | 7/2007 | Ochiai | F22B 37/003 73/627 |
| 2011/0080804 A1 | 4/2011 | Vu et al. | |

FOREIGN PATENT DOCUMENTS

| | | | | |
|---|---|---|---|---|
| EP | 1158283 A1 * | 11/2001 | | G01H 9/00 |
| GB | 1134877 A * | 11/1968 | | G08B 13/194 |
| GB | 1367859 A * | 9/1974 | | G03H 3/00 |
| GB | 1478835 A * | 7/1977 | | G01P 5/18 |
| JP | 02307689 A * | 12/1990 | | |
| JP | 2923779 B1 * | 7/1999 | | |

OTHER PUBLICATIONS

UK IPO Search and Examination Report, UK application No. GB1521095.8, dated May 13, 2016, 4 total pages.
International Search Report, International Searching Authority, pp. 1-11, dated May 28, 2013.

* cited by examiner

ACOUSTIC CAMERA

CROSS-REFERENCE TO RELATED APPLICATIONS

The present application claims the benefit of U.S. Provisional Patent Application No. 61/641,969 for "Acoustic Camera" which was filed on May 3, 2012, the entire content of which is hereby specifically incorporated by reference herein for all that it discloses and teaches.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to imaging devices and, more particularly, to an acoustic camera effective for obtaining 3-dimensional images of objects immersed in optically opaque fluids.

BACKGROUND

During drilling operations for oil and gas, items, such as drilling pipe, drilling collars, casings, logging tools, testing tools, wire line, hand tools, tong parts, slip segments, bit cones, chains, expensive measurement while drilling (MWD) tools, and directional drilling packages, as examples, are often dropped into or forgotten in a wellbore. Once a component is lost, it is properly referred to as a "fish." Therefore, mechanical devices used to aid in the recovery of equipment lost down hole are called fishing tools.

Generally, items introduced into a wellbore are accurately measured and sketched, so that appropriate fishing tools can be selected if the item must be fished out of the hole and diagnostic tools are required. Optical digital cameras may be used for wells which are optically clean. However, wells do not often contain clean fluids and must be flushed with water before images can be taken, a process which may several days, thereby increasing the cost of the fishing operation. Therefore, industry practice is to leave mud in the pipe during fishing operations. Some cameras use lenses to which surfactants have been applied to the surface to allow imaging through hydrocarbons that are transparent. However, there are currently no imaging devices available that allow imaging through mud (oil or water based).

In such situations, an impression block made of soft metal, usually lead, is dropped onto the fish so that upon subsequent inspection, generally on the surface, a custom tool may be designed to facilitate attachment to and retrieval of the fish.

Although fishing occurs frequently, most fishing tasks are relatively simple and the lost time is confined to that of operating the fishing tool and retrieving the fish. However, the impression block technique does not always provide adequate information, and some jobs become costly and time consuming, resulting on occasion in the loss of the hole. It has been estimated that fishing operations account for 25% of drilling costs worldwide.

SUMMARY OF THE INVENTION

Embodiments of the present invention overcome the disadvantages and limitations of the prior art by providing an apparatus for generating an accurate 3-dimensional image of an object immersed in an optically opaque liquid.

Another object of embodiments of the present invention is to provide an apparatus for generating an accurate 3-dimensional image of an object immersed in an optically opaque liquid in approximately real time.

Yet another object of embodiments of the present invention is to provide an apparatus for generating an accurate 3-dimensional image of an object immersed in mud.

Still another object of embodiments of the present invention is to provide an apparatus for generating an accurate 3-dimensional image of an object immersed in mud in a wellbore.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for obtaining a 3-dimensional image of an object hereof, includes: a broadband piezoelectric transducer for generating and transmitting ultrasonic pulses onto the object; a pulse generator for providing electrical signals to the transducer; an ultrasonic detector effective for receiving ultrasonic pulses in a 2-dimensional pattern and for producing electrical signals in response to ultrasound impinging thereon; an acoustic lens for receiving acoustic pulses reflected from the object and focusing the ultrasonic pulses onto the acoustic detector; and digital signal processing electronics for receiving the electrical signals from the acoustic detector in a 2-dimensional pattern and for generating a 3-dimensional image therefrom using the time-of-flight of the reflected acoustic pulses at each location in the 2-dimensional pattern, and for controlling the pulse generator.

In another aspect of the present invention and in accordance with its objects and purposes, the apparatus for obtaining a 3-dimensional image of an object hereof, includes: a broadband piezoelectric transducer for generating and transmitting ultrasonic pulses; a 2-dimensional segmented piezoelectric acoustic receiver array for producing electrical signals in response to acoustic pulses impinging thereon; a partially transmitting acoustic mirror for reflecting acoustic pulses from the transducer onto the object; a compound acoustic lens disposed between the partially transmitting mirror and the receiver array for receiving reflected acoustic pulses from the object passing through the partially transmitting mirror, and for focusing the reflected pulses onto the receiver array; and digital signal processing electronics for receiving the electrical signals from the receiving array and for generating the 3-dimensional image from the time-of-flight of the reflected acoustic pulses at each segment of the acoustic receiver.

In yet another aspect of the present invention and in accordance with its objects and purposes, the apparatus for obtaining a 3-dimensional image of an object hereof, includes: a broadband ultrasonic piezoelectric film transducer for generating and transmitting ultrasonic pulses onto the object; a pulse generator for providing electrical signals to the transducer; a 2-dimensional segmented piezoelectric acoustic detector array for producing electrical signals in response to ultrasound impinging thereon; a compound acoustic lens for receiving acoustic pulses reflected from the object and focusing the ultrasonic pulses onto the piezoelectric film transducer through which the ultrasonic pulses continue to the acoustic detector, said compound lens comprising a fixed acoustic focusing lens nearest the object, a movable focusing acoustic lens, and means for moving the movable acoustic focusing lens to achieve a chosen magnification of the compound acoustic lens; and digital signal processing electronics for receiving the electrical signals from the acoustic detector in a 2-dimensional pattern and for generating a 3-dimensional image therefrom using the time-of-flight of the reflected acoustic pulses at each location in the 2-dimensional pattern, for controlling said means for moving the movable acoustic lens, and for controlling the pulse generator.

Benefits and advantages of embodiments of the present invention include, but are not limited to, providing an apparatus for generating a 3-dimensional image of an object submerged in an optically opaque fluid in approximately real-time using sound frequencies less than about 800 kHz, and with a depth resolution of less than about 1 mm, as well as in other fluids, in a confined environment, such as a tube. In addition to other applications, such images may enable appropriate fishing tools to be selected for retrieval of downhole objects.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of an embodiment of the acoustic camera of the present invention for obtaining 3-dimensional images of an object from acoustic time-of-flight measurements on a segmented 2-dimensional acoustic detector, while

DETAILED DESCRIPTION OF THE INVENTION

Figure 1A:
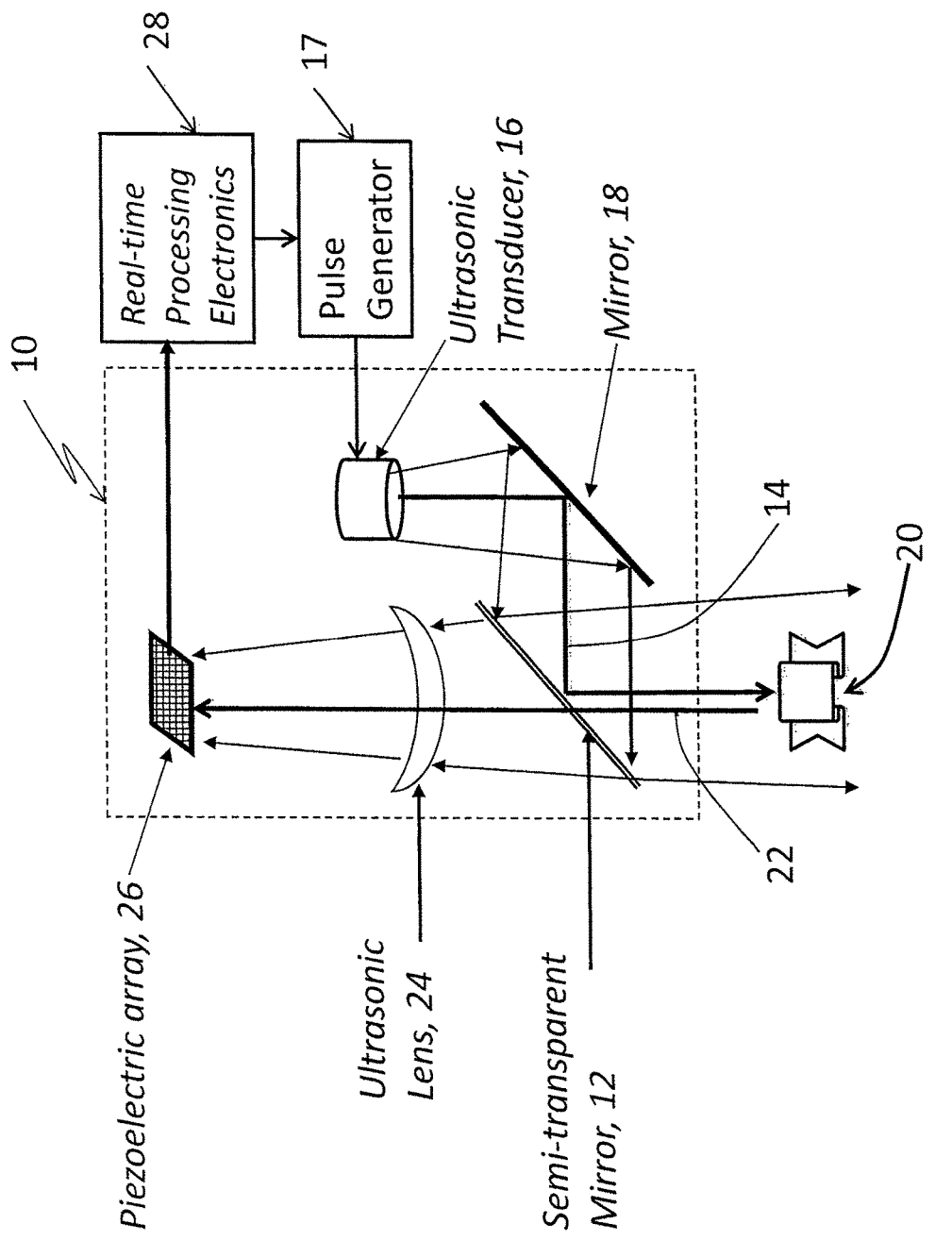

Embodiments of the present invention include an apparatus for generating accurate 3-dimensional images of objects immersed in liquids including optically opaque liquids which may also have significant sound attenuation. Sound pulses having frequencies less than about 800 kHz, and advantageously between about 100 kHz and about 700 kHz, are caused to impinge on the object, and the time-of-flight of sound reflected from the object is used to create a 3-dimensional image of the object in almost real-time. The sound image may be displayed on a computer screen. In addition, the image can be translated into a 3-dimensional object using an inexpensive 3-dimensional printing device. In situations where an identification of a fish immersed in mud after having been dropped in a well bore is required, the 3-dimensional recreation of the object can be used to determine an appropriate fishing tool for retrieval. Since the present apparatus is capable of creating images of objects immersed in fluids that are optically opaque and may have high sound attenuation, the apparatus will have applications other than as fishing diagnostic tool.

If an object is illuminated by either ambient light or by another light source (for example, a flashbulb), or by a combination thereof, and the light scattered from the object is focused by a lens and recorded on a 2-dimensional CCD chip, one may obtain a two-dimensional image. Typically, the intensity of reflected light and the wavelengths of the light on each pixel are recorded to produce a color picture. For embodiments of the acoustic imaging camera of the present invention, the object is first insonified (flooded with pulsed sound waves), and the scattered waves are directed through an acoustic lens and digitized by a 2-dimensional array of piezoelectric elements where each element converts the received acoustic signal to an electric signal. When the electrical output of the array is electronically processed, an image of the object is created from the time-of-flight of the sound pulses on each pixel of the array.

For down hole and other applications, depth information from the object is sought, whereby the final image can be transformed into a three-dimensional representation. This information can be displayed as 3-dimensional object. Embodiments of the present acoustic camera are effective for capturing acoustic images inside pipes which are filled with optically opaque, but ultrasonically attenuating fluids, such as mud, oil, and the like, through which light cannot penetrate, at depth resolutions less than about 1 mm.

Because of the inaccessibility of objects in confined environments, such as in tubes and well bores, diagnostic insonification is achieved from the same side of the object as the acoustic lens and the 2-dimensional detector array. In order to accomplish this in an effective manner and, as will be described in detail hereinbelow, a polyvinylidene difluoride (PVDF) film that permits collinear insonification of an object and the detection of reflected or scattered sound pulses by the object on a 2-dimensional detector array with a high-degree (approximately 95%) of sound transmission therethrough, is used.

Embodiments of the apparatus of the present invention may view an object from between approximately the front surface of the enclosure containing the ultrasonic camera and about 2 ft away therefrom in mud. The distance between lenses and detectors in the present apparatus is thus comparable to the object distance. By contrast, commercial sonic imaging systems are generally designed for object distances that are much greater than the distance between lenses and receivers, with the exception of the Acoustocam i600 from Imperium, Inc. The Acoustocam uses a large transmitter with an acoustic partial mirror to transmit plane waves, which artificially simulate an object at a distance that is very large, as opposed to the use of spreading waves, which renders this camera incapable of producing images of objects that are wider than the lens. Further the Acoustocam is stated as being able to image only 1 in.$^2$ at a time, which is approximately the area of the lens used in the Acoustocam system. Embodiments of the present invention, by contrast, can image objects that are up to three-times the width of the lenses employed. Additionally, the Imperium system operates at high frequencies which cannot penetrate mud.

As stated hereinabove, sound waves are used to image objects at relatively short distances (about 2 ft. away), over relatively wide angles, fluid attenuation must be considered. Since sound attenuation is proportional to the square of the frequency, lower frequencies are more effective for penetrating fluids at this distance. For penetrating mud with a typical PVDF transmitter, frequencies between about 100 kHz and about 800 kHz have been found to be effective, depending on the penetration depth needed. However, higher frequencies may be used to achieve the same penetration depth if the transmitter is capable of producing higher output power. At lower frequencies, diffraction becomes important to the design of lenses. The angular resolution of a lens is given by:

$$\sin\theta = 1.22\left(\frac{\lambda}{D}\right),$$

where θ is the half-angle width of the focal point produced by the lens, λ is the wavelength of sound at the frequency used, and D is the diameter of the lens. For a given lens diameter, then, lower frequencies decrease image focusing. Therefore, frequencies are chosen to be sufficiently high to prevent lens diffraction from becoming an important issue, but low enough to permit acceptable fluid penetration. When using the present acoustic camera for imaging objects submerged in fluids, this compromise permits usable images to be obtained for objects about 2 ft. away from the camera.

Wellbore applications further require that the lenses are narrower than the object to be imaged, by about a factor of three. The inner diameter of a typical borehole is about 6 in., while the acoustic camera must be lowered through a 2-in. diameter hole in the drill bit. This requires that the lenses be about a factor of three narrower than the object to be imaged, and also requires that the lenses focus the image of a 6-in. wide object onto a receiver array that is about 2-in. wide; that is, the lenses should have a magnification factor of about one-third. The distance between the lenses and the detector are comparable to the object distance, because magnification=−(image distance/object distance), in contrast with other acoustic imaging systems that use lenses designed to image objects at distances that are much greater than the distance between lenses and receivers. Although down hole imaging in highly attenuating fields requires a magnification of about one-third, the lens system may be designed with magnifications required by other applications as well.

Thin lenses have lower acoustic attenuation, which directs the use of larger radii of curvature when designing lens surfaces, because sound will be attenuated more towards the edges of the lens than at the center (where the lens is thinnest). If this effect is not compensated for, the ability of the lens to focus sound may be compromised. Large radii of curvature lenses also require that the distance between the lenses and detectors to be comparable to the object distance, as stated hereinabove. For these conditions, the depth-of-field (the ranges of distance over which acceptable focus is achieved when a lens system is focused at a particular distance) produced by a lens system is given by DOF=cf (m+1)/(rm$^2$), where f is the distance between the lenses and the detectors, m is the magnification of the lens system, r is the radius of the lenses (that is, the distance from the center of the lens to the outer edge thereof), and c is the maximum allowable focal point width. For the present embodiments, m=⅓, f=7, r=1, and c=1.5 mm, the width of the individual detector array elements. This results in a depth-of-field of about 18 mm. If the lens system is to produce focused images of objects with greater than 18 mm depth-of-field, an adjustable-focus system is used. Because of the relatively short object distance, the depth-of-field of the lens system (the range of distance over which the lens can produce an acceptably focused image) is short, which requires an adjustable-focus system, rather than a fixed-focus system. With an adjustable-focus system, a group of images is obtained, each focused at a different distance, the images then being composited to form a final image having a large final depth-of-field. A clearly focused image in 3-dimensions over the chosen distances is produced thereby. The combination of relatively close objects with off-axis imaging generates considerable field curvature (the image created behind the lens is produced on a curved surface rather than a flat plane, even if the object is flat), which can be reduced to an acceptable level through the use of multiple lenses and careful design.

Figure 5:
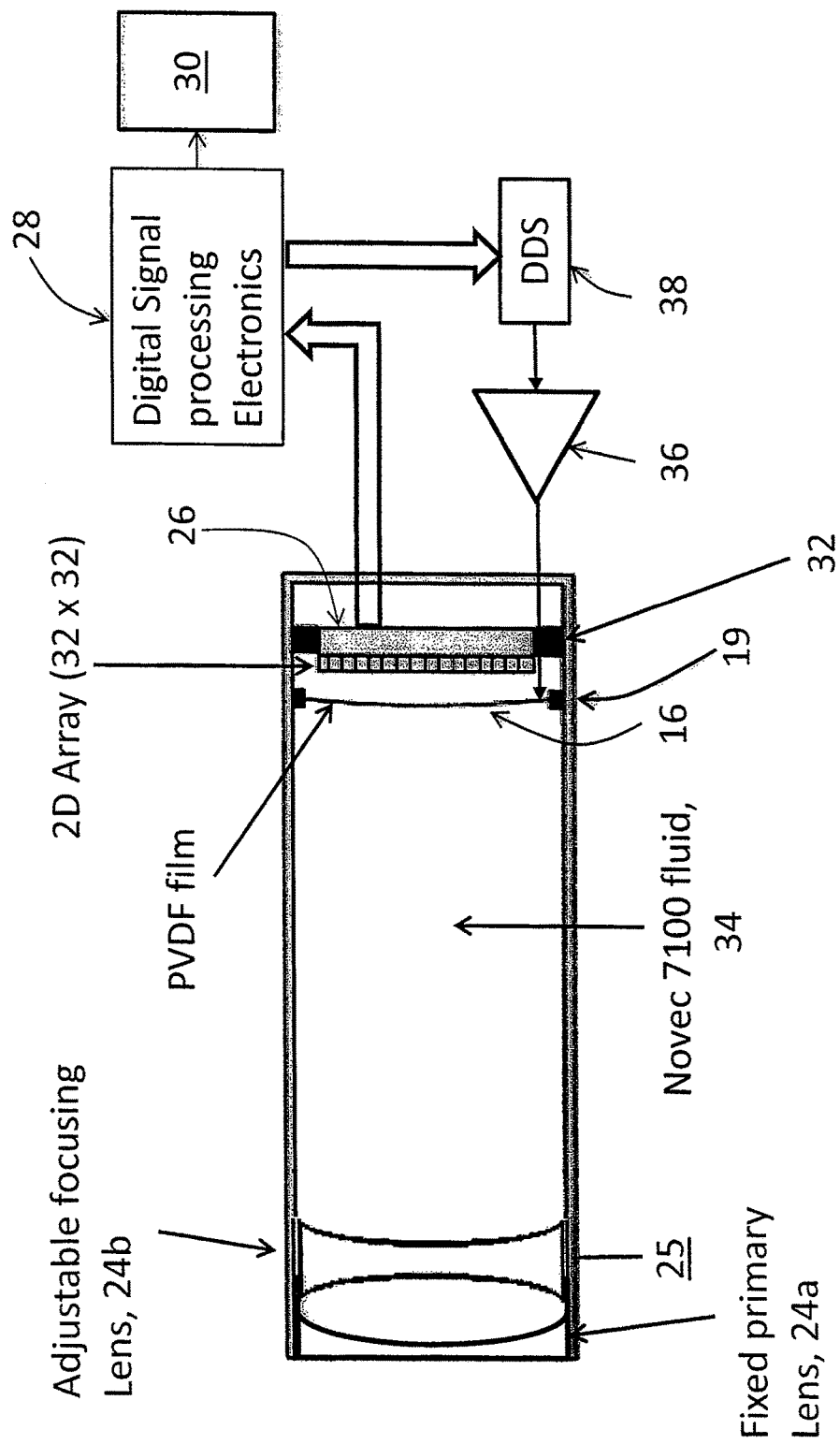
FIG. 5 is a schematic representation of the embodiment of the acoustic camera shown in FIG. 4 hereof, illustrating the placement of the components of the camera in a cylindrical housing suitable for well bore deployment and containing a sound-communicating fluid.

The primary lens is plano-concave, as illustrated in FIG. 5, hereinbelow. The surface facing the exterior of the camera may be planar since the index of refraction of that surface of the lens depends on the fluid in which the camera is submerged. The index of refraction is given by the ratio of the sound speed in the lens to that in the fluid. Crude oil may have a different sound speed than drilling mud, for example (and different types of crude may have different sound speeds, etc.), and the index of refraction of the lens at the outer surface may be changed. If this surface were curved, the focal length of the lens would depend on the fluid outside the camera, which would require a change in the position of the receiving array. In practical terms, this would require that the camera be adjusted and calibrated for different conditions in which it is used. In addition, if physical conditions within the borehole cause a change in sound speed (for example, the temperature and/or the composition of the fluid changes, as examples), the camera may drift out of focus unless some dynamic calibration mechanism were in place. By making the external surface flat, it does not contribute to the focusing effect of the lens, thereby negating any effects due to a changing sound speed in the fluid outside the camera, and maintaining a fixed receiver array position within the camera.

The curved surface of the primary lens was chosen to have a radius of curvature of about 7 in., while the two curved surfaces of the secondary lens were both chosen to have a radius of curvature of about 20 in. However, these radii may be different for different requirements, and it is not required that the two surfaces of the secondary lens have the same radius of curvature; nor is it required that either of the lenses be spherical lenses. Lenses may be chosen to be aspheric or aplanatic, as examples.

Figure 1B:
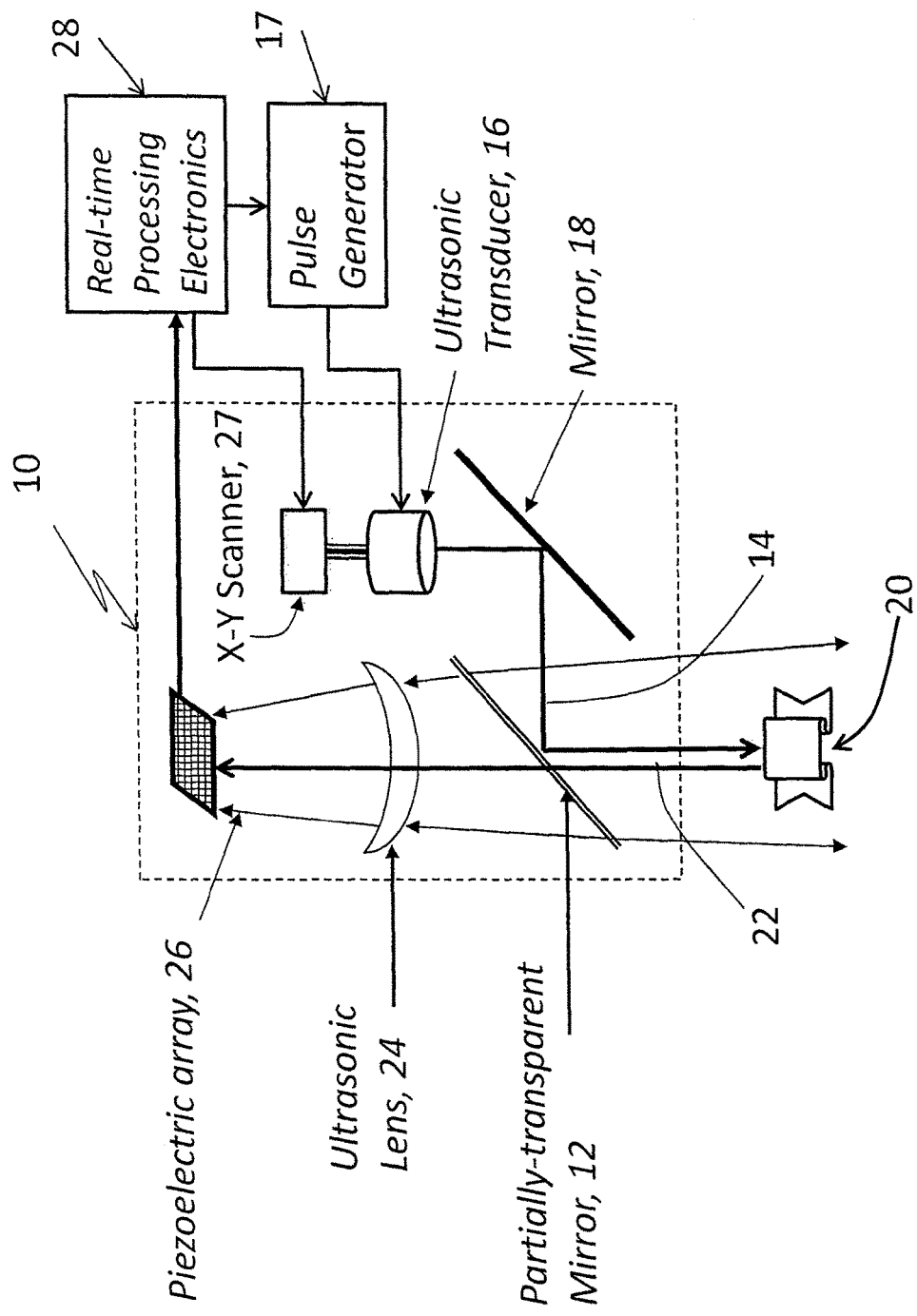
FIG. 1B is a schematic representation of the camera shown in FIG. 1A hereof illustrating apparatus for scanning the pulsed ultrasonic transducer in 2-dimensions for illuminating the object.

Reference will now be made in detail to the present embodiments of the invention, examples of which are illustrated in the accompanying drawings. In the FIGURES, similar structure will be identified using identical reference characters. It will be understood that the FIGURES are presented for the purpose of describing particular embodiments of the invention and are not intended to limit the invention thereto. Turning now to FIG. 1A, an embodiment of acoustic camera, 10, of the present invention is shown. Partially reflecting/partially transmitting acoustic mirror, 12, directs sound beam, 14, reflected from ultrasonic transducer, 16, driven by pulse generator, 17, by mirror, 18, to object, 20. Partially reflecting mirror 12 may be fabricated from a thin metal plate, and mirror 18 may be a metal plate. Reflected and scattered sound, 22, from object 20 passes through partially reflecting mirror 12, is focused by acoustic (ultrasonic) lens, 24, onto means, 26, for detecting a 2-dimensional sound pattern. Detection means 26 may include a 2-dimensional array of piezoelectric transducers. The source of sound beam 14 may include conventional ultrasonic transducers, or a parametric array transducer driven by a pulse generator, a tone burst generator or a frequency chirp generator. Parametric array transducers provide a broadband (extending from approximately 50 kHz to about 1 MHz) frequency range, but collimated (divergence <2°) beam, wherein the frequency range can be varied. Two high-frequency electrical signals (for example, one at 5 MHz and the other swept between 4 and 5 MHz) are applied to a piezoelectric disc transducer in a small cylinder (2 cm in diameter and 2 cm in length) filled with a nonlinear medium, such as Fluorinert FC-43 (3M Company), wherein a difference frequency is generated. This difference frequency has a broad bandwidth, but is highly collimated. Although for borehole applications, the typical beam divergence of a transducer suffices for illuminating the object, parametric array transducers which, as will be described hereinbelow, provide the larger bandwidths effective for chirp frequency excitation for obtaining highly accurate time-of-flight information, have much smaller divergences. Although one may introduce a slight concave curvature to mirror 18 in the direction of transducer 16 to increase the divergence of the illuminating beam for ordinary transducers, for parametric array transducers, X-Y (2-dimensional) scanning stage, 27, is employed as illustrated in FIG. 1B. Timing and processing electronics, 28, controls pulse generator 17, to provide electrical pulses to transducer 16, thereby generating a pulsed acoustic output, controls the scan direction and speed of translational apparatus, 27, receives the electronic signals from detector 26, analyzes the electronic signals in real time at each transducer location in the 2-dimensional detector array, recording thereby a time-of-flight measurement, and generates a 3-dimensional image of object 20.

Other means for obtaining a 3-dimensional image include using a single receiver transducer element and scanning it in the X-Y plane, or a linear array of receiver transducer elements and electronically scanning the image along a line (for example, in the X-direction), followed by sequential small shifts in an orthogonal direction (for example, in the Y-direction), with an electronic scan of the image along each new line to obtain a complete image. As stated above, a 2-dimensional array of transducer elements that is electronically scanned in both X and Y directions to obtain the image may also be used.

Figure 4:
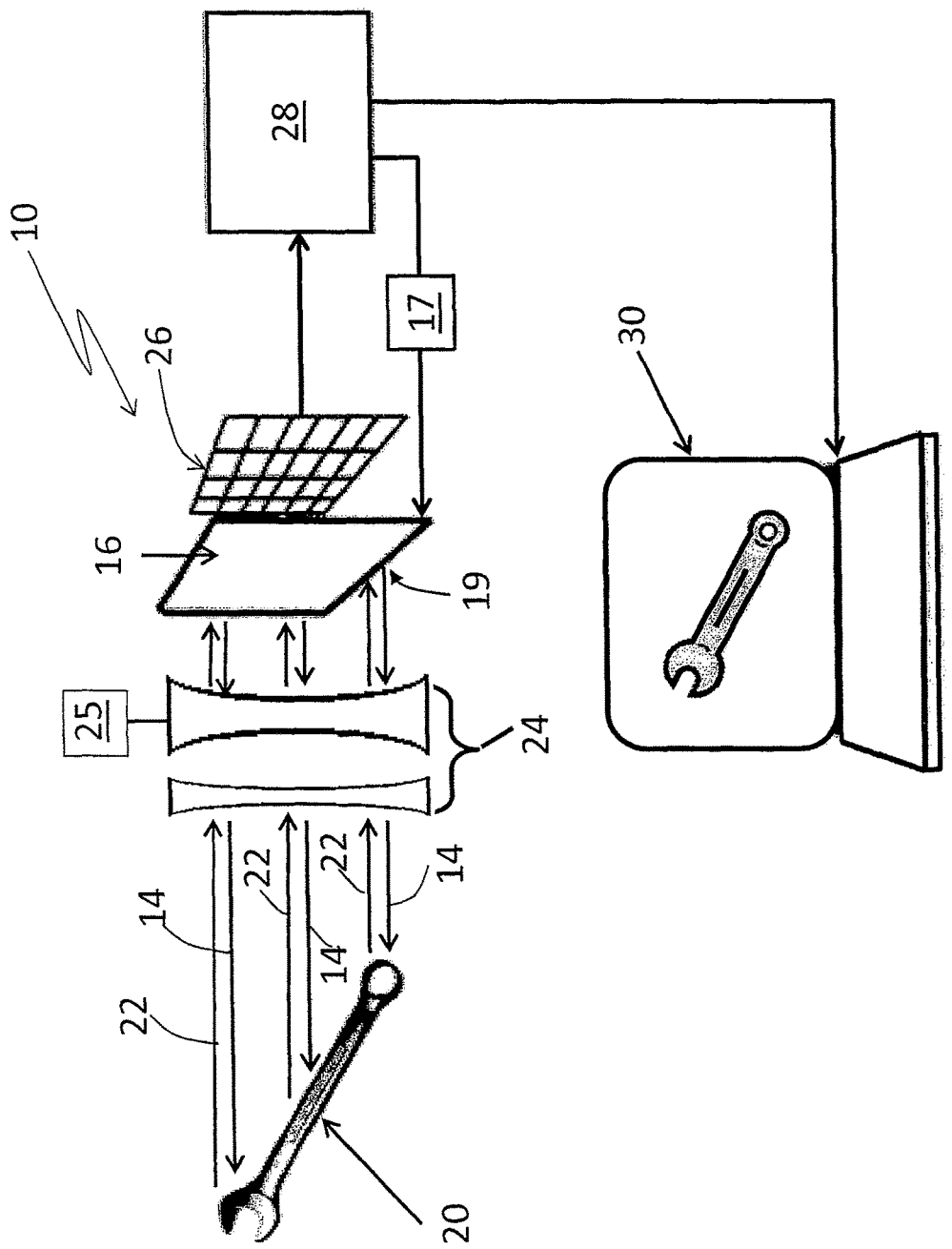
FIG. 4 is a schematic representation of another embodiment of the acoustic camera of the present invention, illustrating the components and the acoustic beam in a linear configuration, which is a consequence of the use of a Polyvinylidene difluoride (PVDF) film as a piezoelectric transducer for generating the acoustic beam.

It should be mentioned that all embodiments of the present acoustic camera when used in boreholes or other harsh environments, are disposed in a tubular or another shape of housing, 32, shown in FIG. 5, but not in FIGS. 1 and 4, hereof for protecting the components. Suitable housings permitting generated acoustic pulses to impinge on the object, and reflected acoustic pulses therefrom to be received and detected by the camera components.

Figure 2:
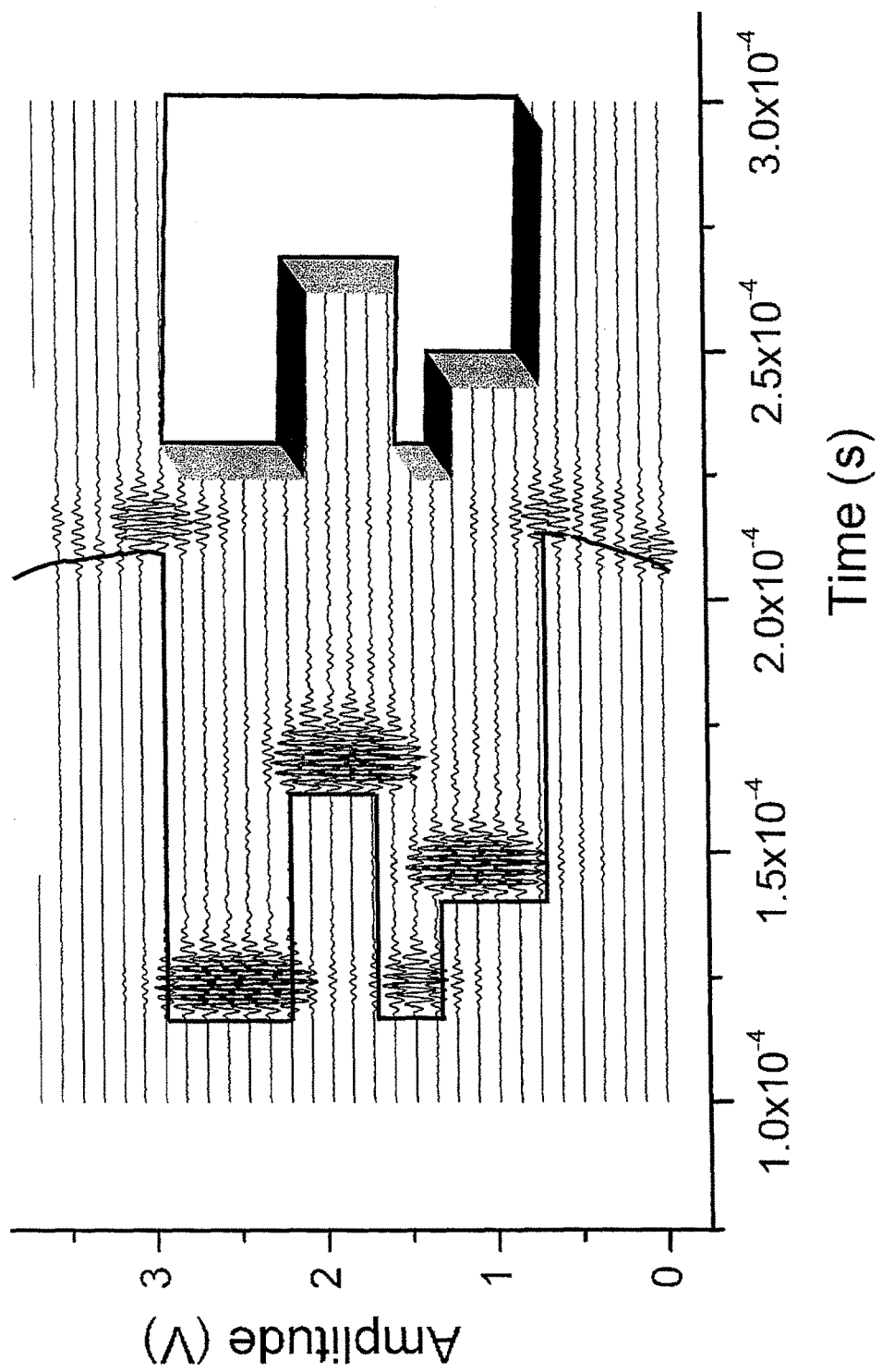
FIG. 2 is graph of a measurement of the time-of-flight for ultrasonic tone bursts reflected from a cross-section of the object shown in the box to the right of the FIGURE using a single pass of a mechanically-scanned piezoelectric receiver over the object, from which a 2-dimensional contour image of the object is obtained.

FIG. 2 is a measurement of the time-of-flight for ultrasonic tone bursts reflected from the object shown in the box to the right of the FIGURE using a single pass (one dimension) of the output of a mechanically-scanned piezoelectric transducer over the object. The first reflected acoustic signal to arrive at the detector (time from insonification to being recorded by the receiver transducer after reflection) is extracted from the measurement to create a 2-dimensional contour image of the object.

Figure 3:
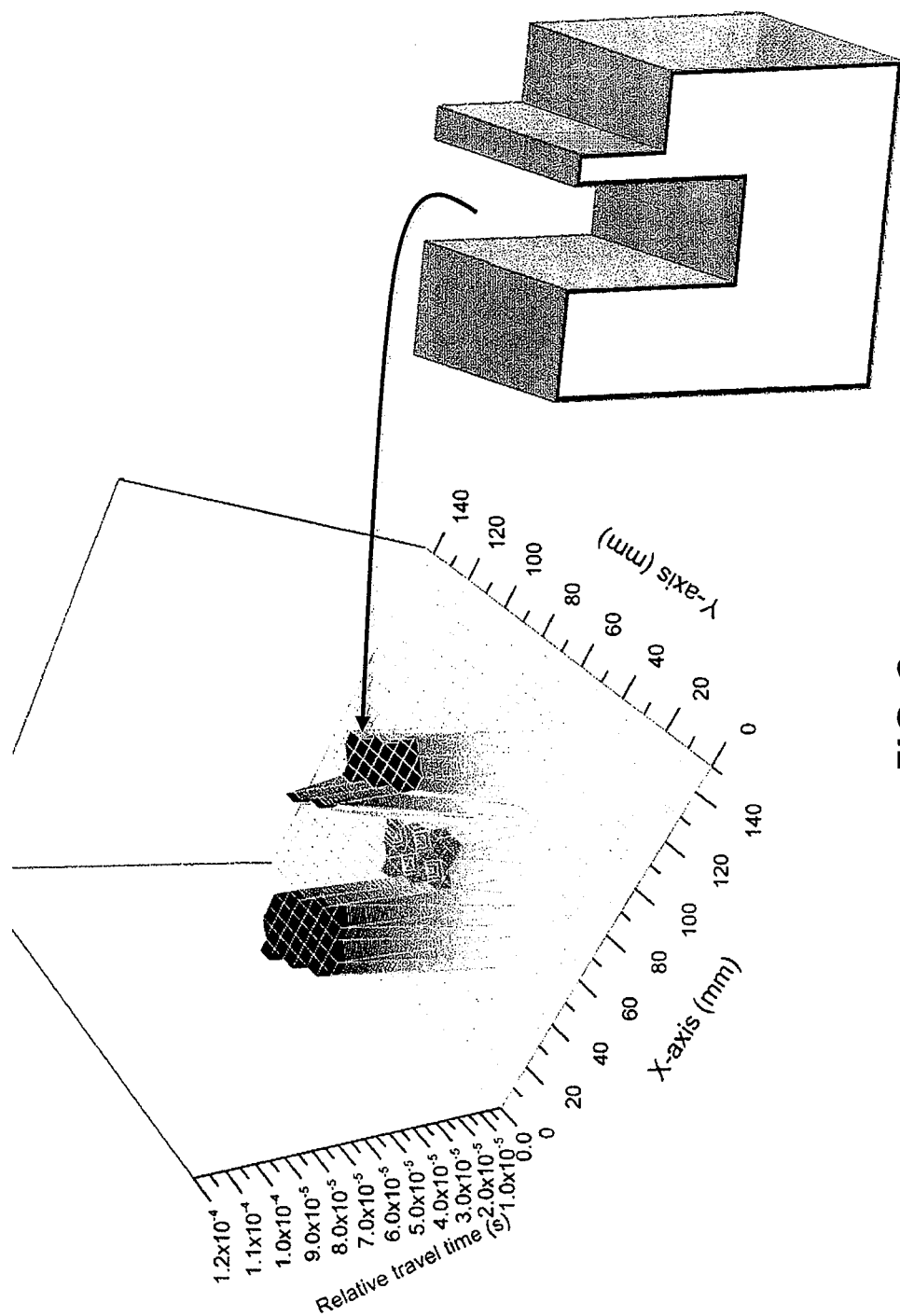
FIG. 3 is a graph of a measurement of the time-of-flight for ultrasonic frequency chirp signals reflected from a cross-section of the object shown in the box to the right of the FIGURE using a 2-dimensional X-Y scan of a mechanically-scanned piezoelectric receiver over the object, from which a 3-dimensional contour image of the object is obtained.

FIG. 3 is a measurement of the time-of-flight for ultrasonic frequency chirp signals reflected from the object shown in the box to the right of the FIGURE using a 2-dimensional X-Y scan of the output of a mechanically-scanned piezoelectric transducer over the object. The first reflected acoustic signal to arrive at the detector is extracted from the measurement to create a 3-dimensional contour image of the object. As will be described in more detail hereinbelow, the higher resolution illustrated in FIG. 3 over that for FIG. 2 hereof, derives from a more accurate determination of the time of arrival of the acoustic signals achieved by using a frequency chirp signal and cross-correlating the transmitted signal with the signal from the receiver. The image was obtained using a 500 kHz parametric beam having a bandwidth of between 100 and 800 kHz, a scanning step size of 5 mm, and a pencil-type ultrasonic transducer.

FIG. 4 is a schematic representation of another embodiment of the acoustic camera of the present invention, including compound acoustic lens 24 fabricated from high-density polyethylene, as an example, which produces excellent sound focusing without significant image aberration. Focusing lens, 24a, is fixed in position, while focusing lens, 24b, is movable by motor, 25, or other suitable means for achieving such motion, which may be remotely controlled, whereby a good focus can be achieved by adjusting the separation between the two lenses. Polyvinyl difluoride (PVDF) film transducer 16 is employed as the source of acoustic pulses. For higher frequency operation and for larger diameters of the PVDF film, the beam divergence is smaller and the beam is more collimated.

PVDF film piezoelectric transducer 16, may be supported by frame, 19, and positioned behind lenses 24, although it may be positioned anywhere in camera 10, and generate acoustic beam 14. Film 16 may be attached to lens 24b itself. The time-of-flight of the reflected and scattered sound from object 20 is detected on 2-dimensional segmented piezoelectric receiving array 26, the electrical output of which is directed to digital signal processing electronics 28. The output from digital signal processing electronics 28 may be processed for viewing and/or stored in computer, 30.

FIG. 5 is a schematic representation of the embodiment of the acoustic camera shown in FIG. 4 hereof, illustrating the placement of the components of the camera in cylindrical camera housing, 32, containing a sound communicating fluid, 34. The PVDF film is driven by output amplifier, 36, which amplifies voltage pulses in the form of either a tone burst or a frequency chirp from direct digital synthesizer, 38, controlled by a microcontroller component of digital signal processing (DSP) electronics 28 to voltages up to 200 V for durations of ≤200 µs. Two-dimensional receiver array 26 may be constructed from a 1 MHz center frequency piezoelectric sheet that is back-loaded to provide a broad frequency band-width (bare piezoelectric material has a narrow resonance, thereby restricting its use to a narrow band of frequencies, and back-loading broadens this range). Since the thickness of the receiver array is determined by the center frequency at which the array is to be operated, the lower the center frequency, the thicker the piezoelectric translator becomes. Therefore, the choice of center frequency determines the thickness of the camera receiver array, and lower center-frequencies require too large a thickness of the piezoelectric-elements in the array to be practicable.

PVDF is a polarizable fluoropolymer having strong piezoelectric properties, and is a flexible, lightweight, tough engineering plastic available in a variety of thicknesses and large areas. As a transducer it has a wide frequency range (0.001 Hz to about $10^9$ Hz); low acoustic impedance (close match to water, human tissue and adhesive systems); high elastic compliance; high dielectric strength (capable of withstanding strong fields (75V/µm) where most piezoelectric ceramics depolarize; high mechanical strength and impact resistance (modulus between about $10^9$ and about $10^{10}$ Pascal); high stability (resists moisture (with <0.02% moisture absorption), most chemicals, oxidants, and intense ultraviolet and nuclear radiation); and can be glued with commercial adhesives. For use as a sound source, thin film electrodes are attached to both sides of the film. For imaging purposes, the sound produced by the transmitter may be omnidirectional in space (equal sound amplitude in all directions), or may be focused in a single beam (like a flashlight beam), as long as the entire object is insonified (beams that are too narrow will insonify only a portion of the object). Of importance is that PVDF films are transparent to sound, which permits sound pulses reflected from an object to pass essentially unimpeded through the film, and be detected by the 2-dimensional detector array behind it. Use of film piezoelectric transducers further permits all components of an embodiment of the present invention to be aligned along a common axis without the requirement of partially transmitting mirrors, which avoids multiple reflections and aberrations.

If the PVDF transducer is located in the vicinity of the receiver array, the transmitted pulse will be focused towards the object to be imaged by the lenses (more like a flashlight beam than a floodlight), while if the PVDF is located away from the receiver array and placed closer to the lenses, the spatial distribution of the pulse will become wider outside the camera. The PVDF film may be treated as a piston source for determining the sound beam profile generated when the film is excited by a voltage source. The angle of the beam can be determined from the following equation:

$$\sin\theta = q\frac{V}{DF}$$

Here, θ=the full beam spread; q=the constant beam divergence factor (0.51 for 6 dB and 1.02 for 12 dB); V=the material velocity (m/µs); D=the transducer crystal diameter (mm); and F=the transducer frequency (MHz).

Sound communicating fluid 34 includes Novec 7100, 3M Company, in which all camera components including internal lens 24b, PVDF film 16, and receiver array 26 are submerged. Any of the Novec or other fluids in the Fluorinert family of fluids (3M Company) may be used. The outer diameter of the camera is 3.75", and the overall length is about 12" in order to be accommodated by typical wellbores. Clearly, other dimensions may be contemplated.

Compound lens 24 is designed to achieve a chosen magnification with the least distortion and lowest attenuation. For an object that is 6 in. wide (for example, the diameter of a typical wellbore) to be imaged onto a receiver array that is 2 in. wide, a lens system having a magnification of one-third is needed. This may be achieved with a single lens; however, for the present application, a single lens would result in unacceptable distortion. A single lens would also give rise to a fixed-focus system, that is, a system that delivers the chosen magnification only for a specific object distance. Therefore, a second lens with an adjustable position relative to the first lens, is added to permit greater radii of curvature to be used for both lenses, thereby reducing distortions, and to permit for adjustable focus capability, while maintaining the chosen magnification. This second lens allows the focus of the dual-lens to be dynamically adjusted, and enables the camera to image objects over the entire range of adjustable focus, providing an additional advantage in the situation where an operator does not have fine control over the position of the camera.

A specific high-density polyethylene plastic (HDPE) is used in the present embodiments since the speed of sound in HDPE is 1980 m/s, while the density is 930 kg/m$^3$. Therefore, the acoustic impedance is 1.84×10$^6$ kg/m$^2$·s, 23% greater than that for water. By contrast, a widely used acoustic lens material is polymethylpentene, which has an acoustic impedance of about 44% greater than that of water; therefore, the HDPE is about a factor of two better than commonly used materials. Greater impedance mismatch introduces greater sound attenuation and sound reflection. However, if attenuation is not important, a metal lens 24a may be used for improving the ability of the apparatus to withstand high external pressures. A combination of a metal (for example, stainless steel) outer lens (fixed) 24a and an inner adjustable HDPE lens 24b may also be used.

Novec 7100 was found to be advantageous as the sound-communicating fluid. First, the acoustic impedance of the fluid, that is, the product of the density (1520 kg/m$^3$) and sound speed (610 m/s), is a good match to that for water (the acoustic impedance of water is about 62% greater). Impedance matching reduces acoustic reflections within the camera which obscure the image, and maximizes signal transmission. Second, this fluid is electrically insulating, which allows the receiver array and its associated electrical connections to be submerged in the fluid without concern for capacitive coupling, and electrical crosstalk, etc. In addition, the fluid is non-corrosive, so that it actually protects the receiver array and its connections. Third, the low sound speed of Novec 7100 (610 m/s) provides an advantage. The wavelength of sound in Novec 7100 (at a chosen frequency) is about ⅓ of what it would be in water. This permits the camera to be constructed about ⅓ as short in length as would otherwise be required. The camera may also be constructed to be about ⅓ the width. As stated hereinabove, the half-angle width of the focal point produced by a lens is given by $\sin(\theta)=1.22\lambda/D$, where λ is the wavelength of sound in the fluid and D is the diameter of the lens. For a chosen frequency, λ, in Novec 7100 is about ⅓ that for water.

Therefore, for a particular focal point half-angle, the lens diameter may be reduced by about a factor of three.

The reduced sound speed of Novec 7100 further increases the index of refraction of the lens; that is, the ratio of the sound speed in the lens (1980 m/s) to that in the fluid (610 m/s), or about 3.25. This, in turn, permits a much greater radii of curvature to be used when designing the lenses (the focal length of a lens with one spherically-curved side is given by $f=R/(n-1)$, where R is the radius of curvature and n is the index of refraction), the benefit being a decrease in spherical aberration, coma, and other distortions inherent in spherical lenses. Other ways to reduce these distortions include the use of lenses that are aspheric and/or aplanatic, which are more difficult and complex to design and fabricate.

Returning to FIG. 5, in operation embodiments of the present invention generate short pulses of sound as tone bursts or frequency chirps by PVDF film 16, depending on the input from DDS 38. Film 16 is collinear with lenses 24 and 2-dimensional piezoelectric receiving array 26, all being aligned inside tubular container 32, which may be constructed from metal or other rugged materials. A thin sheet of another piezoelectric material may also be used in place of the PVDF film. However, as stated hereinabove, because of the excellent acoustic impedance match of the PVDF film material with most fluids including water, ultrasonic signals may pass through the system with almost 98% transmission efficiency without generating multiple reflections at the interfaces. Further, the material is effectively acoustically transparent. Other elements, such as the semi-transparent acoustic mirror 12 shown in FIG. 1, generate multiple reflections. The pulse from PVDF film 16 travels through lenses 24a, 24b into the surrounding fluid or other medium to the object, whereby the sound reflected or scattered by the object returns towards camera 10, enters through compound lenses 24, which focus the pulse through closely acoustically transparent PVDF film 16 and onto receiving array 26. The 2-dimensional receiving array 26 converts the focused sound pulse into electronic signals, which are then processed by signal processing circuitry 28. Fast DSP 28 provides multiple frames of images per second on computer display 30. The processed time-of-flight signals provide depth and intensity information.

Figures 6A, 6B:
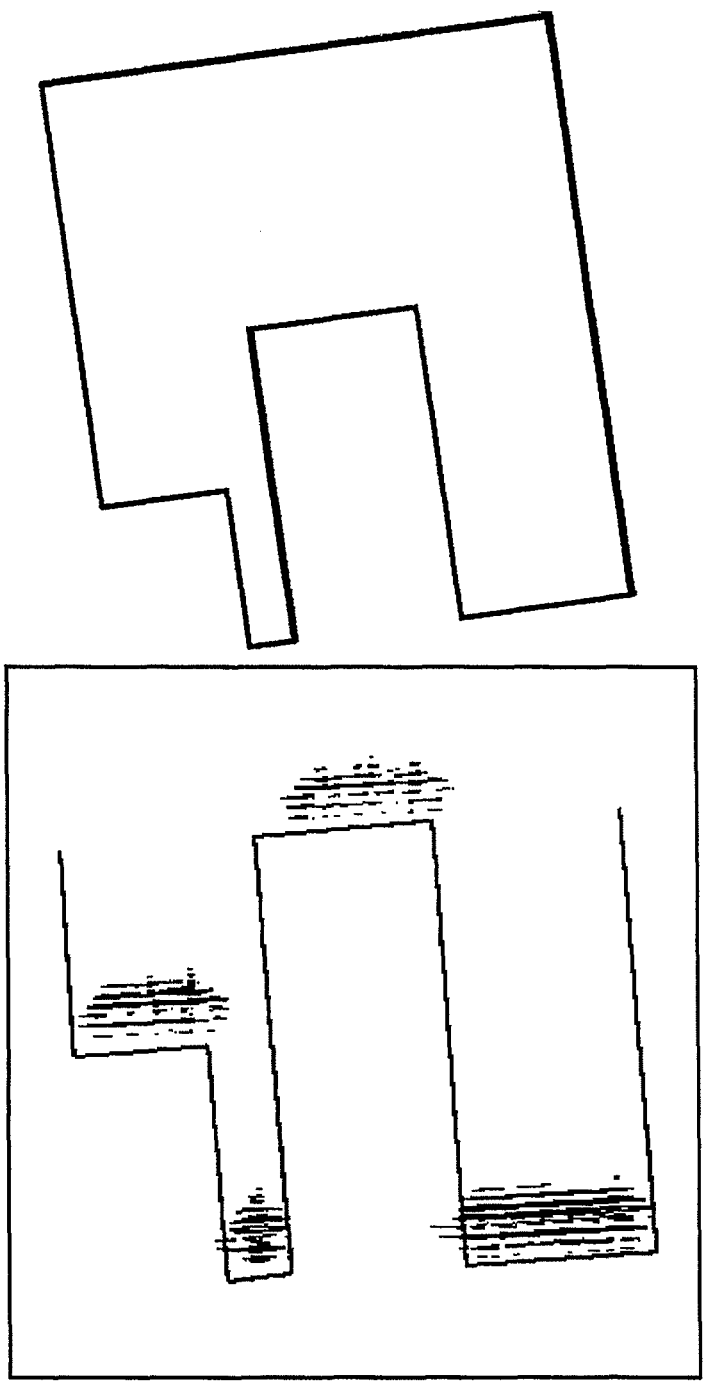
FIG. 6A shows raw data generated from a one-dimensional scan using the embodiment of the apparatus shown in FIG. 4 hereof, of the object shown in FIG. 6B, wherein a tone burst signal is generated by the PVDF film behind the focusing lenses for insonifying the object.

FIG. 6A shows the raw data produced from a one-dimensional scan using the embodiment of the apparatus shown in FIG. 4 hereof with a scanned, single piezoelectric receiver element, of the object shown in FIG. 6B, wherein a tone burst (a few cycles of a sine wave) signal generated by PVDF film 16 behind lenses 24, is used for insonifying the object. Cross-sectional data only is shown for clarity. Object information from the first sound waves to arrive is shown by the line drawn through the data.

More accurate time measurements, with consequent higher resolution images, may be obtained using frequency chirp excitation signals (a short signal that sweeps through a range of frequencies) with subsequent cross-correlation of the excitation signal with the received signal from each element of 2-dimensional array 26, whereby an image similar to that shown in FIG. 3 is obtained.

Figure 7:
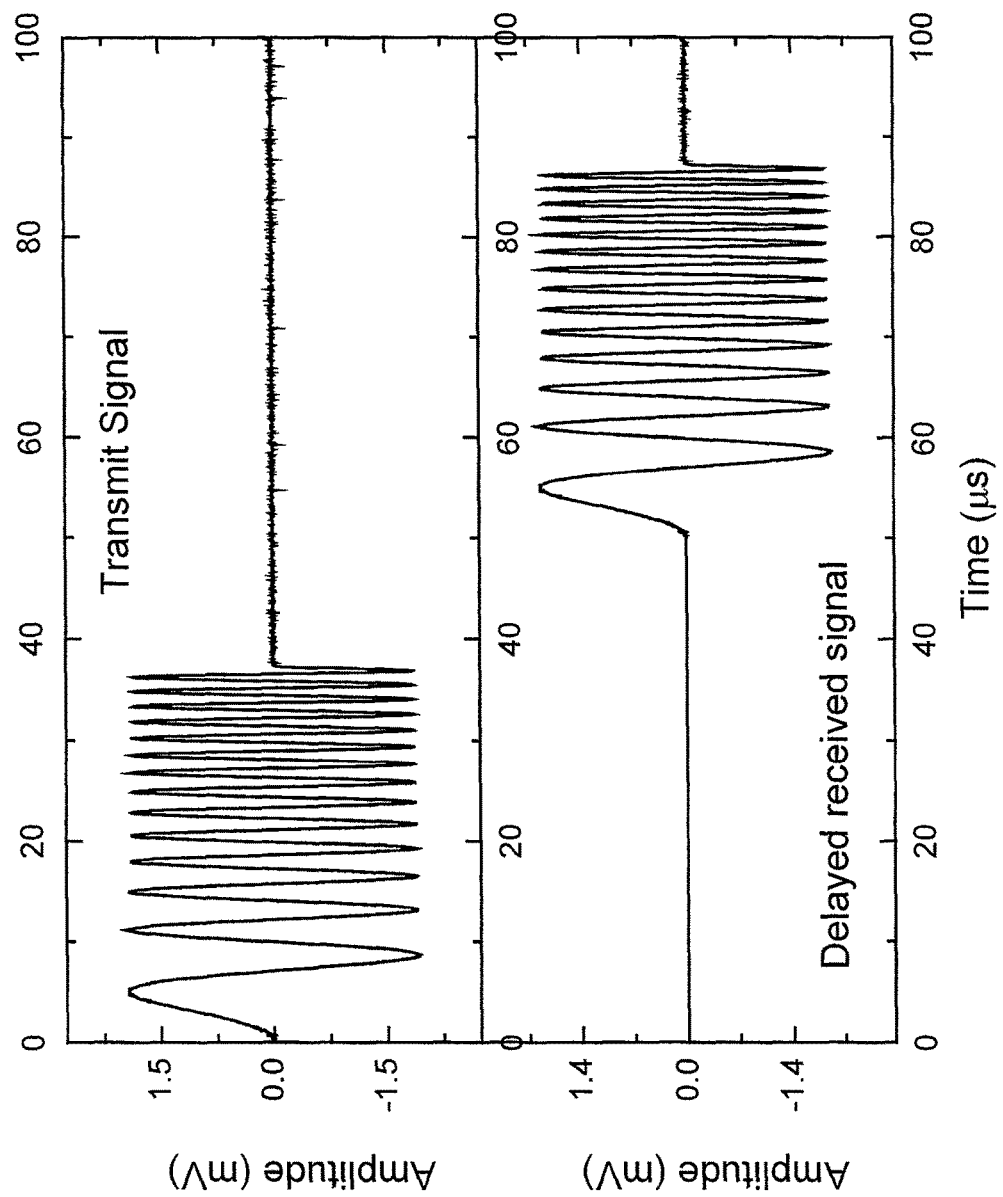
FIG. 7 is a graph of a transmitted frequency chirp signal (upper curve) and a delayed received chirp signal (lower curve) as a function of time in µs.
Figure 8:
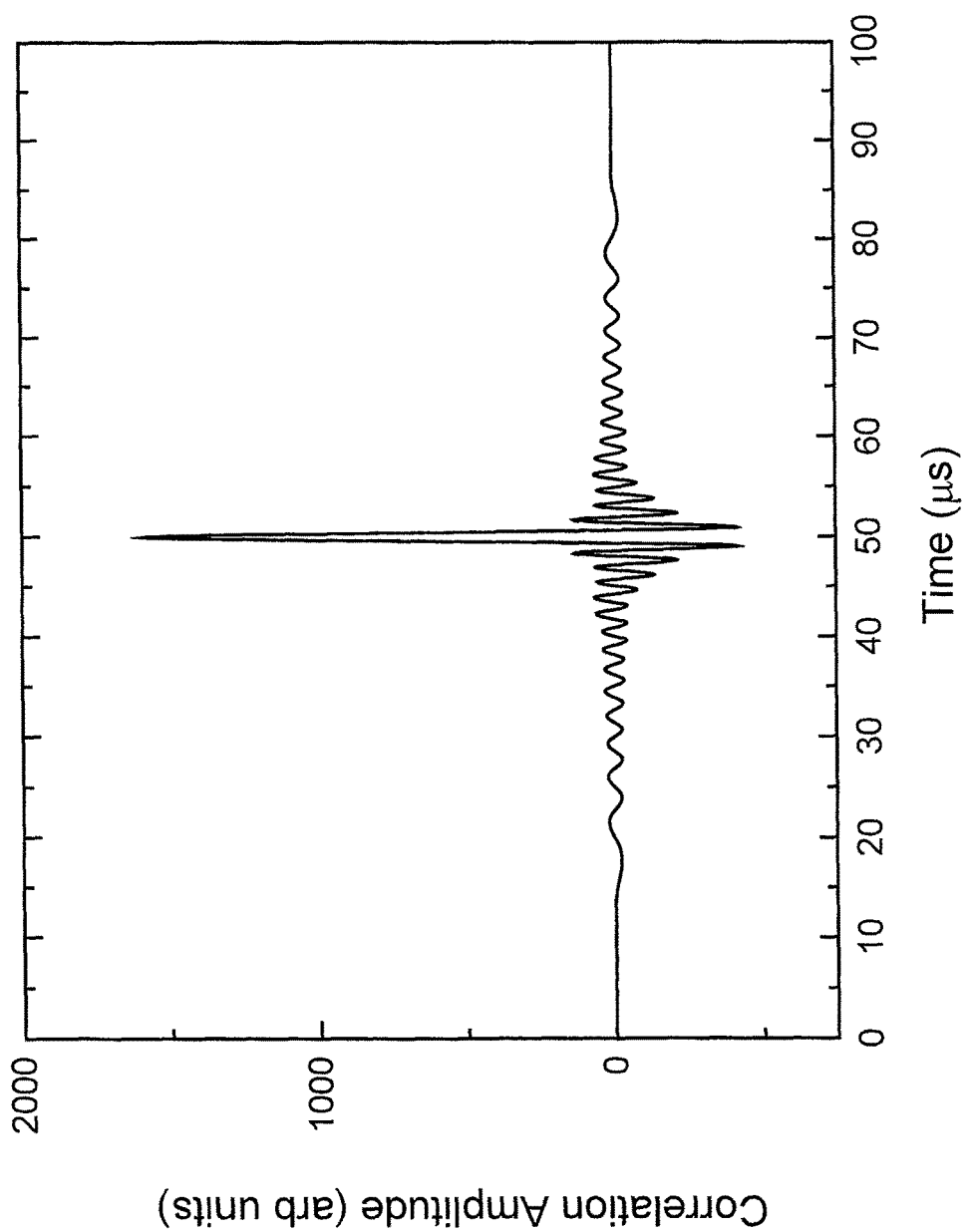
FIG. 8 is a graph of the time-of-flight information derived by cross-correlating the two signals shown in FIG. 7 hereof, where the position of the sharp peak in FIG. 8 yields a more accurate time-of-flight in µs.

A transmitted frequency chirp and a delayed chirp are shown in FIG. 7, while the position of the sharp peak shown in FIG. 8 is the time-of-flight information derived by cross-correlating the two signals in FIG. 7 (transmit and received) through a mathematical process. This results in more accurate time measurement with improved image resolution, than a determination of the delay from a measurement of the starting time for the signal. The accuracy further increases with increasing frequency bandwidth of the frequency chirp. Higher frequencies have shorter wavelengths, which permits distance calculations having higher resolution, and distance divided by sound speed provides the time-of-flight.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for obtaining a 3-dimensional image of an object, comprising: a broadband piezoelectric transducer for generating and transmitting ultrasonic pulses onto said object; a pulse generator for providing electrical signals to said transducer; an ultrasonic detector effective for receiving ultrasonic pulses in a 2-dimensional pattern and for producing electrical signals in response to ultrasound impinging thereon; an acoustic lens for receiving only those acoustic pulses reflected from said object and for focusing the ultrasonic pulses onto said ultrasonic detector; and digital signal processing electronics for receiving the electrical signals from said ultrasonic detector in a 2-dimensional pattern and for generating a 3-dimensional image therefrom using the time-of-flight of the reflected acoustic pulses at each location in the 2-dimensional pattern, and for controlling said pulse generator.

2. The apparatus of claim 1, wherein said piezoelectric transducer comprises a parametric array transducer having a chosen bandwidth.

3. The apparatus of claim 2, wherein the bandwidth of said parametric array transducer extends from about 50 kHz to about 1 MHz.

4. The apparatus of claim 2, further comprising a translation stage controlled by said digital signal processing electronics for moving said transducer over a chosen 2-dimensional pattern.

5. The apparatus of claim 1, wherein said ultrasonic detector comprises a two-dimensional segmented piezoelectric transducer array.

6. The apparatus of claim 1, further comprising a partially transmitting acoustic mirror; and a second mirror for directing acoustic pulses from said piezoelectric transducer to said partially transmitting mirror and onto said object, wherein reflected sound pulses from said object pass through said partially transparent mirror to said acoustic lens.

7. The apparatus of claim 6, wherein said second mirror is concave in the direction of said piezoelectric transducer.

8. The apparatus of claim 1, wherein said partially transmitting mirror comprises a metal plate.

9. The apparatus of claim 1, wherein the ultrasonic pulses generated by said piezoelectric transducer comprise frequency chirp pulses.

10. The apparatus of claim 9, wherein the ultrasonic pulses generated by said piezoelectric transducer are cross-correlated with said electrical signal from said acoustic detector by said digital signal processing electronics.

11. Apparatus for obtaining a 3-dimensional image of an object, comprising: a broadband piezoelectric transducer for generating and transmitting ultrasonic pulses; a 2-dimensional segmented piezoelectric ultrasonic detector array for producing electrical signals in response to ultrasonic pulses impinging thereon; a partially transmitting acoustic mirror for reflecting acoustic pulses from said transducer onto said object; a compound acoustic lens disposed between said partially transmitting mirror and said ultrasonic detector array for receiving reflected acoustic pulses from said object passing through said partially transmitting mirror, and for focusing the reflected pulses onto said ultrasonic detector array; and digital signal processing electronics for receiving the electrical signals from said ultrasonic detector array and for generating the 3-dimensional image from the time-of-flight of the reflected acoustic pulses at each segment of said ultrasonic detector array.

12. The apparatus of claim 11, wherein said piezoelectric transducer comprises a parametric array transducer having a chosen bandwidth.

13. The apparatus of claim 12, wherein the bandwidth of said parametric array transducer extends from about 50 kHz to about 1 MHz.

14. The apparatus of claim 12, further comprising a translation stage controlled by said digital signal processing electronics for moving said transducer over a chosen 2-dimensional pattern.

15. The apparatus of claim 11, further comprising a second mirror for directing acoustic pulses from said piezoelectric transducer to said partially transmitting mirror.

16. The apparatus of claim 15, wherein said second mirror is concave in the direction of said piezoelectric transducer.

17. The apparatus of claim 11, wherein said partially transmitting mirror comprises a metal plate.

18. The apparatus of claim 11, wherein the ultrasonic pulses generated by said piezoelectric transducer comprise frequency chirp pulses.

19. The apparatus of claim 18, wherein the ultrasonic pulses generated by said piezoelectric transducer are cross-correlated with said electrical signal from said ultrasonic detector array by said digital signal processing electronics.

* * * * *